United States Patent [19]

Braun

[11] Patent Number: 5,738,847
[45] Date of Patent: Apr. 14, 1998

[54] ANTI-VH3-15 REAGENTS AND METHODS FOR THEIR USE

[75] Inventor: Jonathan Braun, Encino, Calif.

[73] Assignee: The Regents of the University of California, Oakland, Calif.

[21] Appl. No.: 309,025

[22] Filed: Sep. 19, 1994

[51] Int. Cl.$^6$ .................. A61K 39/395; C12P 21/04; G01N 33/53

[52] U.S. Cl. .................. 424/141.1; 424/131.1; 424/139.1; 435/70.2; 435/70.72; 436/547; 436/548

[58] Field of Search .................. 530/387.1, 387.2, 530/387.5, 388.1, 388.4, 389.1, 389.5, 866; 424/9.34, 131.1, 139.1, 141.1, 144.1, 152.1, 178.1, 809; 436/547, 548; 435/70.2, 70.21, 240.26, 240.27

[56] References Cited

U.S. PATENT DOCUMENTS 5,292,667  3/1994  Podolsky et al. .................. 436/435

FOREIGN PATENT DOCUMENTS 9118628   6/1991  WIPO.
9202819   7/1991  WIPO.
9312248  12/1992  WIPO.

OTHER PUBLICATIONS

Azmi, F.H. et al. Infect. Immun., vol. 62, No. 5, pp. 1776–1786 (May 1994).
Adderson, E.E., et al., "Restricted Ig H Chain V Gene Usage in the Human Antibody Response to *Haemophilus influenzae* Type b Capsular Polysaccharide." *J. Immunol.*, 147: 1667–1674 (1991).
Adderson, E. E., et al., "The Human VH3b Gene Subfamily Is Highly Polymorphic." *J. Immunol.*, 151(2): 800–809 (1993).
Adderson, E. E., et al., "Restricted Immunoglobulin VH Usage and VDJ Combinations in the Human Response to *Haemophilus influenzae* Type b Capsular Polysaccharide. Nucleotide Sequences of Monospecific Anti-Haemophilus Antibodies and Polyspecific Antibodies Cross-reacting with Self Antigens." *J. Clin. Invest.*, 91(6): 2734–2743 (1993).
Andris, J. S., et al., "Molecular Characterization of Human Antibodies to Bacterial Antigens: Utilization of the Less Frequently Expressed $V_H2$ and $V_H6$ Heavy Chain Variable Region Gene Families." *Mol. Immunol.*, 30: 1601–1616. (1993).
Axelrod, O., et al., "Idiotypic Cross–Reactivity of Immunoglobulins Expressed in Waldenström's Macroglobulinemia, Chronic Lymphocytic Leukemia, and Mantle Zone Lymphocytes of Secondary B–cell Follicles." *Blood,* 77: 1484–1490 (1991).
Berberian, L., et al., "Immunoglobulin $V_H3$ Gene Products: Natural Ligands for HIV gp120." *Science,* 261: 1588–1591 (1993).
Blaser, M. J., et al., "Studies of *Campylobacter jejuni* in Patients With Inflammatory Bowel Disease." *Gastroenterology,* 86: 33–38 (1984).

Blaser, M. J., et al., "*Campylobacter jejuni* Outer Membrane Proteins Are Antigenic for Humans." *Infect. Immun.*, 43(3): 986–993 (1984).
Blaser, M. J., et al., "Human Serum Antibody Response to *Campylobacter jejuni* Infection as Measured in an Enzyme–Linked Immunosorbent Assay." *Infec. Immun.*, 44(2): 292–298 (1984).
Blaser, M. J., et al., "Antigenicity of *Campylobacter jejuni* Flagella." *Infec. Immun.*, 53(1): 47–52 (1986).
Braun, J., et al., "Restricted Use of Fetal VH3 Immunoglobulin Genes by Unselected B Cells in the Adult. Predominance of 56p1–like VH Genes in Common Variable Immunodeficiency." *J. Clin. Invest.*, 89: 1395–1402 (1992).
Chamberlain, C. E., et al., "*Campylobacter (Helicobacter) pylori*: Is Peptic Disease a Bacterial Infection?" *Arch. Intern Med.*, 150: 951–955 (1990).
Cook, G. P., et al., "A map of the human immunoglobulin $V_H$ locus completed by analysis of the telomeric region of chromosome 14q." *Nature Genet.*, 7(2): 162–168 (1994).
Das, K.M., et al., "The Production and Characterization of Monoclonal Antibodies to A Human Colonic Antigen Associated with Ulcerative Colitis: Cellular Localization of the Antigen by Using the Monoclonal Antibody." *J. Immunology*, 139: 77–84 (1987).
Das, K. M., et al., "A Shared and Unique Epitope(s) on Human Colon, Skin, and Biliary Epithelium Detected by a Monoclonal Antibody." *Gastroenterology*, 98: 464–469 (1990).
Deane, M., et al., "The Genetic Basis of Human $V_H4$ Gene Family–Associated Cross–Reactive Idiotype Expression in CD5+ and CD5– Cord Blood B–Lymphocyte Clones." *Scand. J. Immunol.*, 38: 348–358 (1993).
Duerr, R. H., et al., "Anti–Neutrophil Cytoplasmic Antibodies in Ulcerative Colitis. Comparison With Other Colitides/Diarrheal Illnesses." *Gastroenterology*, 100: 1590–1596 (1991).
Eggena, et al., "Characterization of a Ulcerative Colitis Specific pANCA Using Phage Display Technology." *F. Am. Soc. Exper. Biol.*, J8(5): A1010 (1994).
Elsaghier, A., et al., "Antibodies to *Mycobacterium paratuberculosis*–specific protein antigens in Crohn's disease." *Clin. Exp. Immunol.*, 90: 503–588 (1992).
Ermel, R. W., et al., Preferential Utilization of a Novel Vlambda3 Gene in Monoclonal Rheumatoid Factors Derived From the Synovial Cells of Rheumatoid Arthritis Patients. *Arthritis Rheum.*, 37(6):860–868 (1994).
Graham, D. Y., "*Campylobacter pylori* and Peptic Ulcer Disease." *Gastroenterology*, 96: 615–625 (1989).

(List continued on next page.)

Primary Examiner—James C. Housel
Assistant Examiner—Rodney P. Swartz
Attorney, Agent, or Firm—Campbell & Flores LLP

[57] ABSTRACT

Anti-VH3-15 idiotypic antibody materials, hybridomas producing this antibody material and methods for using these to detect, isolate and purify VH3-15 polypeptides. Also provided in the present invention are nucleic acid molecules encoding anti-VH3-15 antibody material and methods for using these molecules to detect, isolate and purify VH3-15 nucleic acid sequences.

10 Claims, No Drawings

OTHER PUBLICATIONS

Griffiths, A. D., et al., "Human anti–self antibodies wwith high specificity from phage display libraries." *EMBO J.*, 12: 725–734 (1993).

Huang, C., et al., "A Majority of Ig H Chain cDNA of Normal Human Adult Blood Lymphocytes Resembles cDNA for Fetal Ig and Natural Autoantibodies." *J. Immunol.*, 151: 5290–5300 (1993).

Jefferies, L. C., et al., "Idiotypic Heterogeneity of VkappaIII Autoantibodies to Red Blood Cell Antigens." *Clin. Immunol. Immunopathol.*, 65(2): 119–128 (1992).

Johnson, R. J., et al., "Persistent *Campylobacter jejuni* Infection in an Immunocompromised Patient." *Ann. Intern. Med.*, 100: 832–834 (1984).

Jonusys, A. M., et al., "IgM Natural Autoantibodies Against Bromelain–Treated Mouse Red Blood Cells Recognize Carbonic Anhydrase." *Autoimmunity*, 9: 207–216 (1991).

Kearney, J. F., "Idiotypic Networks." *Fundamental Immunology.* 3 ed. Paul, W. New York: Raven Press; 1993; c. 1993: 887–902. (Paul, W.). ISBN: 0–7817–0022–1.

Kipps, T. J., et al., "Uniform High Frequency Expression of Autoantibody–Associated Crossreactive Idiotypes in the Primary B Cell Follicles of Human Fetal Spleen." *J. Exp. Med.*, 171: 189–196 (1990).

Kipps, T. J., et al., "Autoantibodies in Chronic Lymphocytic Leukemia and Related Systemic Autoimmune Diseases." *Blood*, 81: 2475–2487 (1993).

Langman, R. E., et al., "The 'complete' idiotype network is an absurd immune system." *Immunol. Today*, 7: 100–101 (1986).

Lindberg, E., et al., "Antibody (IgG, IgA, and IgM) to baker's yeast (*Saccharomyces cerevisiae*), yeast mannan, gliadin, ovalbumin, and betalactoglobulin in monozygotic twins with inflammatory bowel disease." *Gut*, 33: 909–913 (1992).

Lydyard, P. M., et al., "The Antibody Repertoire of Early Human B Cells. III. Expression of Cross–Reactive Idiotopes Characteristic of Certain Rheumatoid Factors and Identifying VkappaIII, $V_HI$, and $V_HIII$ Gene Family Products." *Scand. J. Immunol.*, 32: 709–716 (1990).

Lynch, R.G., "Myeloma Proteins and Cells: Monoclonal Tools in the Analysis of Immunoregulatory Mechanisms." *Hybridoma*, 3: 60 (1984).

MacKenzie, L. E., et al., "Repertoire of CD5+ and CD5– cord blood B cells: specificity and expression of $V_HI$ and $V_HIII$ associated idiotypes." *Clin. Exp. Immunol.*, 88(1): 107–111 (1992).

Mageed, R. A., et al., "Selective Expression of $V_HIV$ Subfamily of Immunoglobulin Genes in Human CD5+ B Lymphocytes from Cord Blood." *J. Exp. Med.*, 174: 109–113 (1991).

Matsuda, F., et al., "Structure and physical map of 64 variable segments in the 3' 0.8–megabase region of the human immunoglobulin heavy–chain locus." *Nature Genetics*, 3: 88–94 (1993).

Modlin, R. L., et al., "Type 2 cytokines and negative immune regulation in human infections." *Curr. Opinion Immunol.* 5: 511–517 (1993).

O'Mahony, S., et al., "Systemic and mucosal antibodies to klebsiella in patients with ankylosing spondylitis and Crohn's disease." *Ann. Rheum. Dis.*, 51: 1296–1300 (1992).

Pascual, V., et al., "Human Immunoglobulin Heavy–Chain Variable Region Genes: Organization, Polymorphism, and Expression." *Adv. Immunol.*, 49: 1–74 (1991).

Paul, W. E., et al., "Regulatory idiotopes and immune networks a hypothesis." *Immunol. Today*, 3: 230–234 (1982).

Pei, Z., et al., "Identification, Purification, and Characterization of Major Antigenic Proteins of *Campylobacter jejuni.*" *J. Biol. Chem.*, 266(25): 16363–16369 (1991).

Sanz, I., et al., "Nucleotide Sequences of Eight Human Natural Autoantibody $V_H$ Regions Reveals Apparent Restricted Use of $V_H$ Families." *J. Immunol.*, 142(11): 4054–4061 (1989).

Saxon, A., et al., "A distinct subset of antineutrophil cytoplasmic antibodies is associated with inflammatory bowel disease." *J. Allergy Clin. Immunol.*, 86: 202–210 (1990).

Siegel, D. L., et al., "Expression and Characterization of Recombinant Anti–Rh(D) Antibodies on Filamentous Phage: A Model System for Isolating Human Red Blood Cell Antibodies by Repertoire Cloning." *Blood*, 83(8): 2334–2344 (1994).

Stevens, T. R., et al., "Anti–Endothelial Cell Antibodies in Inflammatory Bowel Disease." *Digestive Dis. and Sci.*, 38: 426–432 (1993).

Stewart, A. K., et al., "Immunoglobulin V Regions and the B Cell." *Blood*, 83(7): 1717–1730 (1994).

Tao, M., et al., "Idiotype/granulocyte–macrophage colony–stimulating factor fusion protein as a vaccine for B–cell lymphoma." *Nature*, 362: 755–758 (1993).

Tomlinson, I. M., et al., "The Repertoire of Human Germline $V_H$ Sequences Reveals about Fifty Groups of VH Segments with Different Hypervariable Loops." *J. Mol. Biol.*, 227: 776–798 (1992).

Valles–Avoub, et al., "Characterization of a Common VH3–15 Autoantibody Relating Inflammatory Bowel Disease and *C. jejuni* Enterocolitis." *F. Am. Soc. Exper. Biol.*, J. 8(5): A1010 (1994).

Van Spreeuwel, J. P., et al., "Campylobacter colitis: histological immunohistochemical and ultrastructural findings." *Gut*, 26: 945–951 (1985).

Ward, E.S., et al., "Binding activities of a repertoire of single immunoglobulin variable domains secreted from *Escherichia coli.*" *Nature*, 341: 544–546 (1989).

Yamamura, M., et al., "Defining Protective Responses to Pathogens: Cytokine Profiles in Leprosy Lesions." *Science*, 254: 277–279 (1991).

Yang, H., et al., "Ulcerative Colitis: A Genetically Heterogeneous Disorder Defined by Genetic (HLA Class II) and Subclinical (Antineutrophil Cytoplasmic Antibodies) Markers." *J. Clin. Invest.*, 92: 1080–1084 (1993).

Young, F., et al., "Molecular Analysis of a Germ Line–Encoded Idiotypic Marker of Pathogenic Human Lupus Autoantibodies." *J. Immunol.*, 145: 2545–2553 (1990).

Adderson, E. E., et al., "Development of the Human Antibody Repertoire." *Pediatr. Res.*, 32: 257 (1992).

Cleveland, D. W., et al., "Peptide Mapping by Limited Proteolysis in Sodium Dodecyl Sulfate and Analysis by Gel Electrophoresis." *J. Biol. Chem.* 252: 1102 (1977).

Lesavre, P., et al., "Atypical Autoantigen Targets of Perinuclear Antineutrophil Cytoplasm Antibodies (P–ANCA): Specificity and Clinical Associations." *J. Autoimmunity* 6: 185–195 (1993).

Perdigoto, R., et al., "Frequency and significance of chronic ulcerative colitis in severe corticosteroid–treated autoimmune hepatitis." *J. Hepatology* 14: 325–331 (1992).

Warny, M., et al., "Anti–neutrophil antibodies in chronic hepatitis and the effect of α–interferon therapy." *J. Hepatology* 17: 294–300 (1993).

ANTI-VH3-15 REAGENTS AND METHODS FOR THEIR USE

I. ACKNOWLEDGEMENT

This invention was made with support under grant numbers DK46763 and CA12800 from the National Institute of Health. Accordingly, the U.S. Government has certain rights in the invention.

II. BACKGROUND OF THE INVENTION

A. The Antibody Repertoire

Over a lifetime, a person confronts the possibility of infection with an almost infinite number of unique foreign substances (antigens). Since it could never be anticipated which of these antigens will ultimately infect a person, it is beneficial that the body possesses an elegant system of producing an equally infinite array of antibodies which recognize, bind and trigger the destruction of antigens.

Antibodies are Y-shaped, tetrameric molecules consisting of a pair of identical, relatively long polypeptide chains called heavy (H) chains and a pair of identical, shorter polypeptide chains called light (L) chains. Each arm of the Y shaped structure is comprised of one light chain and one end of a heavy chain bound together by a single disulfide bond. At the juncture of the arms, the two heavy chains are bound to each other by two disulfide bonds to form the stem of the Y shaped structure.

This architectural description of an antibody, although visually appealing, can be deceptively simplistic. Antibody architecture accommodates a wealth of structural diversity. Both the heavy and light chains contain variable (V) and constant regions. Since V regions are responsible for antigen binding, the vast array of antibody specificities depends on the diversity in the primary sequence of the V region. Heavy and light chain variable regions (VH and VL) each consist of B-sheet scaffold, surmounted by three antigen-binding loops (complementarity-determining regions or CDRs) of different lengths which are fleshed with a variety of side chains. The CDRs are the most diverse regions of the antibody molecule; all six associate to form the antigen-binding site. The structural diversity of the loops can create binding sites of a variety of shapes, ranging from almost flat surfaces to deep cavities.

Underpinning the structural diversity of antibodies is a combinatorial genetic diversity. Heavy and light chain polypeptides are each encoded by an ensemble of gene segments selected from immunoglobulin (Ig) gene complexes. During the maturation of B-cell (the cells which produce antibodies), discontinuous gene segments within these gene complexes undergo a series of somatic rearrangements to form the nucleic acid sequence that ultimately may encode the heavy and light chains of the antibody molecule.

Generally, the first Ig gene rearrangements occur within the Ig heavy chain gene complex. The VH region is generated by the assembly of a VDJ exon from three separate germline DNA segments. One or more diversity (D) gene segments (selected from more than two dozen D germline gene segments) is joined with a single joining (JH) gene segment (selected from about six functional JH germline gene segments). The resulting DJH complex may then rearrange with a VH gene segment to form a VDJ exon that may encode the variable portion of the antibody heavy chain. About 120 germline VH gene segments (of which only about 80 are potentially functional) are available for Ig gene rearrangement and can be divided into at least six families in the basis of nucleotide homology of 80% or above. After successful VDJ rearrangement, a similar rearrangement occurs to produce the light chain.

Two of the CDRs (1 and 2) are encoded by the VH segment. CDR3, the CDR in direct contact with antigen during antigen-antibody binding, is the most variable portion of the antibody molecule and is encoded by the 3'end of the VH gene segment, the D segment and the 5' end of the JH segment. With nucleotide addition (N-region diversity at the VH-D and D-JH junctions) the use of different reading frames in the D segment, and the combination of different rearranged heavy and light chains, the diversity of primary antibody libraries is huge. During an immune response, the antibody variable regions are further diversified by somatic hypermutation, leading to higher affinity binding of the antigen.

Contrary to what was first believed, the variable region of an antibody can bind more than one epitope and some can bind more than one epitope at the same time. This observation has led to the revision of the original definition of an antibody idiotype as a rarely expressed antigenic determinant on immunoglobulins. In contemporary terms, "idiotope" has come to be used to define V-region-associated structures that can be detected using monoclonal anti-idiotypic antibodies. It follows then that an idiotype of a given immunoglobulin molecule can be described as a collection of idiotopes as mapped by a panel of monoclonal anti-idiotopic antibodies, a conventional cross-absorbed polyclonal anti-idiotype antibody, binding of defined antigens or any combination of these.

B. Autoantibodies

The monumental repertoire of the adaptive immune system has evolved to allow it to recognize and ensnare virtually any shaped microbial molecule either at present in existence or yet to come. However, in doing so it has been unable to avoid the generation of antibodies (autoantibodies) which bind with the body's own constituents and trigger an immunological path of destruction.

Natural immunological tolerance mechanisms prevent the expanded production antibodies with self specificities. After antibody gene rearrangement, virgin B-cells (the cells that generate antibodies) may display antibodies with self-reactivity, but tolerance mechanisms can lead to their deletion or to their energy. Despite this safety-net, autoantibodies are still produced and for many people create no recognizable pathogenic disorder. It has been estimated that 10–30% of B cells in normal, healthy individuals are engaged in making autoantibodies. Production of autoantibodies is not only the result of an exceptionally diverse immune system, an immune response against self can also arise in autoimmune disease or after infections.

C. Anti-Idiotypic Markers

Despite the tremendous potential for diversity, evidence is accumulating which would suggest that V gene segment use is not random. For example, expression of different VH gene families does not reflect the size of the family, nor are functional members of any given family expressed equally. Although some VH gene segments are polymorphic, certain genes appear to be remarkably conserved among unrelated individuals.

Recently a great deal of attention has been directed at investigating this hypothesis that there is programmed use of certain V genes in normal human B cell ontogeny and in autoimmune and neoplastic B cell disorders. However, the present techniques of screening cDNA therefor cumbersome and suffer the shortcomings of the PCR.

Novel clonal markers that are specific for human immunoglobulins of defined VH or VL gene products would provide a reliable and quick means for screening B cell populations for the expression of specific VH and VL idiotypes. They would also readily permit the identification of trends in the use of particular VH segment in pathogenic immune responses as compared to healthy immune responses. Such clonal markers might ultimately prove useful as diagnostic markers of disease states associated with a particular use of VH segment. Even more advantages would be the development of clonal markers that do not compete or sterically interfere with binding of antigen to the antibody. If we are to move forward with our understanding of the immunological system compositions and methods must be developed to allow for convenient, reliable and efficient purification of antibodies on the basis of variable segment utilization.

III. BRIEF DESCRIPTION OF THE INVENTION

In accordance with the present invention, there is provided novel antibody material having specificity for the variable heavy chain region of a VH3-15 polypeptide. This antibody material may take the form of antibody molecules or portions thereof. The antibody material may be polyclonal or monoclonal. Monoclonal anti-VH3-15 idiotypic antibodies are specifically provided and hybridomas for their product are taught.

This novel antibody material may be used in the kits and assay, purification and isolation methods of the present invention. Employing the kits methods of the present invention, the presence, absence or amount of VH3-15 polypeptide in a sample can be detected. VH3-15 polypeptides can also be purified and isolated using the methods of the present invention. Also provided are isolated nucleic acid molecules encoding the anti-VH3-15 idiotypic antibody material of the present invention. These nucleic acid molecules may be used as probes for detecting the presence, absence or amount of nucleic acid encoding anti-VH3-15 idiotypic antibody material in a sample. These nucleic acid molecules may also be used in the kits of the present invention.

IV. DETAILED DESCRIPTION OF THE INVENTION

The monumental repertoire of the adaptive immune system has evolved to allow it to recognize and ensnare virtually any shaped microbial molecule either at present in existence or yet to come. Underpinning the structural diversity of antibodies is an elegant system of combinatorial genetic diversity in which an ensemble of gene segments are joined together and subjected to mutation to produce a unique binding site with high affinity for one or more antigens. Although great strides have been made in recent years at understanding this mechanism of diversity, the tools of research have limited investigators' progress.

The present invention provides powerful immunological tools useful for screening large populations or particular antibodies, B cells or other polypeptides for the VH3-15 idiotype. These tools will allow investigators to associate the use of particular VH segments with particular pathogenic immune responses as compared to healthy immune responses and can serve as markers for locating and isolating antigen. The present invention also provides powerful tools for the isolation and purification of VH3-15 polypeptides.

Traditionally, VH gene segments that cross-hybridize by Southern filter hybridization under standard conditions (0.1X saturated sodium citrate, 0.1% sodium dodecyl sulfate, 65 degrees celcius) are considered members of the same gene family, whereas those VH gene segments that do not cross hybridize under these conditions are members of a distinct VH gene family. In practical terms this means approximately 80% nucleotide sequence homology places two genes within the same family and less than 70% nucleotide sequence homology classifies molecules as belonging to separate VH families. The VH3 gene family is presently considered to have the largest membership.

Recently, VH gene families have been subdivided into sub-families based upon homology to a germline sequence within a VH gene family. VH germline sequences have been mapped and the nomenclature for the sub-families reflects the locus of the germline gene segment. Thus, VH3-15 refers to the fifteenth VH segment from the 3' end of the human Ig heavy chain locus. See, Matsuda, et. al., *Nature Genetics*, 3:88–94 (1993) incorporated herein by reference. The nucleic acid sequence of the VH3-15 gene segment is available on Genbank. The VH3-15 gene segment is also known as M26, 20 pl, DP-38 and 9-1.

The term "VH3-15 nucleic acid sequence" as used herein refers the nucleic acid sequence of a member of the VH3-15 sub-family. A nucleic acid sequence is a member of the VH3-15 sub-family if it has at least 92% nucleotide sequence homology with the VH3-15 germline gene segment. SEQ ID NO. 1, the nucleic acid sequence of 9-1 as reported in Pascual, et al, *Ad. Immun.*, 49:1–74 (1991) incorporated herein by reference, is provided as a representative example of a VH3-15 nucleic acid sequence. The nucleic acid sequence encoding LJ86 (SEQ ID NO. 4) is available on Genbank Accession No. M82929 and is also representative of a VH3-15 nucleic acid sequence. Additional VH3-15 nucleic acid sequences can be found in the published literature. See for example, Braun, et al., *J. Clin. Invest.*, 89:1395–1402 (1992), incorporated herein by reference.

A "VH3-15 polypeptide" refers to a polypeptide sequence that encodes a member of the VH3-15 sub-family. A polypeptide sequence is a member of the VH3-15 sub-family if it is encoded by a VH3-15 nucleic acid sequence or if its CDR1 and CDR2 regions share at least 90% sequence homology with the CDR1 and CDR2 regions of SEQ ID NO. 3. SEQ ID NO. 2, 3 and 4 are representative of VH3-15 polypeptides. Thus, VH3-15 nucleic acids and VH3-15 polypeptides may be encoded as part of larger sequences. For example, a VH3-15 polypeptide may take the form of an antibody ("VH3-15 antibody"), an antibody fragment ("VH3-15 (F(ab')$_2$" or "VH3-15 polypeptides.Fab") or the like. LSF2 anti-*Haemophilus influenzae* type b capsular polysaccharide antibody is another polypeptide representative of a VH3-15 sub-family.

In one embodiment of the invention there is provided, antibody material having immunoreactivity with a variable heavy chain segment of a VH3-15 polypeptide. Such antibody material may be referred to as "anti-VH3-15 idiotypic" antibody material and includes, for example, antibody material and monoclonal antibody molecules produced by hybridomas specifically identified in Example I as BK1, BK2, BK3, BK4, BK5, and BK7, as well as antibody material that bind the same idiotope as the monoclonal antibody molecules produced by these hybridomas.

The term "antibody" or "antibody material" in its various grammatical forms is used herein as a collective noun that refers to an antibody molecule and immunologically active portions of an antibody molecule, i.e., molecules that contain an idiotope.

The term "antibody molecule" in its various grammatical forms as used herein refers to an intact immunoglobulin molecule.

An "idiotope" in its various grammatical forms is used herein to refer to any portion of the variable region (heavy and light chain variable and hypervariable regions) of an antibody molecule that is capable of binding an antibody or an antigen. An "epitope" in its various grammatical forms is used herein refers to any portion of an antigen that is capable of binding an antibody. The word "epitope" will be reserved for use herein only to refer to antigenic determinants on non-immunoglobulin antigens.

Exemplary antibody material useful in the compositions and methods of the present invention are intact immunoglobulin molecules, substantially intact immunoglobulin molecules and those portions of an immunoglobulin molecule that contain an idiotope, including those portions known in the art as Fab, Fab', F(ab')$_2$ and F(v). Fab and F(ab')$_2$ portions of antibodies are prepared by the proteolytic reaction of papain and pepsin, respectively, on substantially intact antibodies by methods that are well known in the art. See, for example, U.S. Pat. No. 4,342,566 to Theofilopolous and Dixon incorporated herein by reference. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

Antibody immunoreactivity with VH3-15 polypeptides can be measured by a variety of immunological assays known in the art, as described for example in Harlow and Lane, *Antibodies: A Laboratory Manual* (Cold Spring Harbor Laboratory 1988) incorporated herein by reference. Exemplary immunoreaction of an anti-VH3-15 idiotypic antibody with a VH3-15 polypeptide is described in Example II.

Anti-VH3-15 idiotypic antibodies of either monoclonal or polyclonal form can be produced using techniques presently known in the art. For example, polyclonal and monoclonal antibodies can be produced as described, for example, in Harlow and Lane, *Antibodies: A Laboratory Manual* (Cold Spring Harbor Laboratory 1988), which is incorporated herein by reference. Altered antibodies, such as chimeric, humanized, CDR-grafted or bifunctional antibodies can also be produced by methods well known to those skilled in the art. Such antibodies can also be produced by hybridoma, chemical or recombinant methodology described, for example in Ausubel et al., *Current Protocols in Molecular Biology* (Greene Publishing Associates, Inc. and John Wiley & Sons, Inc. 1993), also incorporated herein by reference.

Exemplary methods of making and isolating monoclonal anti-VH3-15 idiotypic antibodies are provided in Examples I and II. The phrase "monoclonal antibody" in its various grammatical forms refers to a population of antibody molecules that contain only one species of idiotope capable of immunoreacting with a particular epitope on an antigen or idiotope on an antibody. A monoclonal antibody typically displays a single binding affinity for an epitope or idiotope with which it immunoreacts; however, a monoclonal antibody may be a molecule having a plurality of idiotopes, each immunospecific for a different epitope or idiotope, e.g., a bispecific monoclonal antibody.

Monoclonal antibodies are typically composed of antibodies produced by clones of a single cell called a hybridoma that secretes (produces) but one kind of antibody molecule. In accordance with the present invention hybridomas capable of producing antibody material having specific immunoreactivity with the variable heavy chain segment of a VH3-15 polypeptide is provided. Such hybridomas include, for example, BK1, BK2, BK3, BK4, BK5, and BK7, specifically described in Example I. One of skill in the art will recognize that the hybridomas disclosed herein can be used to produce other immortal cell lines that produce antibody material of the present invention.

A hybridoma cell is formed by fusing an antibody-producing cell and a myeloma or other self-perpetuating cell line. The preparation of such hybridomas was first described by Kohler and Milstein, *Nature*, 256:495–497 (1975), which description is incorporated by reference. Polypeptide-induced hybridoma technology is also described by Niman et al., *Proc. Natl. Sci., U.S.A.*, 80:4949–4953 (1983), which description is also incorporated herein by reference.

To obtain an antibody-producing cell for fusion with an immortalized cell, a mammal is inoculated with an immunogen. The word "immunogen" in its various grammatical forms is used herein to describe a composition containing a VH3-15 polypeptide as an active ingredient used for the preparation of the antibodies against VH3-15 polypeptides. When a polypeptide is used in an immunogen to induce antibodies, it is to be understood that the polypeptide can be used in various embodiments, e.g., alone or linked to a carrier as a conjugate, or as a polypeptide polymer or as a fusion protein for ease in purification. For a VH3-15 polypeptide that contains fewer than about 35 amino acid residues, the peptide may be bound to a carrier, for the purpose of inducing the production of antibodies.

The amount of VH3-15 polypeptide immunogen used to inoculate the mammal should be sufficient to induce an immune response to the immunizing polypeptide. This amount depends, among other things, on the species of animal inoculated, the body weight of the animal and the chosen inoculation regimen as is well known in the art. Inocula typically contain about 10 micrograms of immunogen per inoculation for mice and may contain up to about 500 milligrams of immunogen per inoculation for larger mammals.

The spleen cells of the mammal immunized with a VH3-15 polypeptide are then harvested and can be fused with myeloma cells using polyethylene glycol (PEG) 1500. Fused hybrids are selected by their sensitivity to HAT. Hybridomas producing an anti-VH3-15 idiotipic monoclonal antibody can be identified by screening hybridoma supernates for the presence of antibody molecules that immunoreact with VH3-15 polypeptide. Such screening methods include for example, radioimmunoassay (RIA) or enzyme linked immunosorbent assay (ELISA).

A monoclonal antibody of the present invention can also be produced by initiating a monoclonal hybridoma culture comprising a nutrient medium containing a hybridoma that secretes anti-VH3-15 idiotypic antibody molecules. The culture is maintained under conditions and for a time period sufficient for the hybridoma to secrete the antibody molecules into the medium. The antibody-containing medium is then collected. The antibody molecules can then be further isolated by well known techniques.

Other methods of producing a monoclonal antibody, a hybridoma cell, or a hybridoma cell culture are also well known. See, for example, the method of isolating monoclonal antibodies from an immunological repertoire as described by Sastry et al., *Proc. Natl. Acad. Sci.,*

86:5728–5732 (1989); and Huse et al., *Science*, 246:1275–1281 (1981), both of which are incorporated herein by reference.

Media useful for the preparation of these compositions are well known in the art and commercially available and include synthetic culture media, inbred mice and the like. An exemplary synthetic medium is Dulbecco's minimal essential medium (DMEM; Dulbecco et al., *Virol.*, 8:396 (1959)) supplemented with 4.5 gm/l glucose, 20 mm glutamine, and 20% fetal calf serum. An exemplary inbred mouse strain is the Balb/c.

The anti-VH3-15 idiotypic antibody materials so produced can be used in the methods of the present invention to detect the presence, absence or amount of VH3-15 polypeptide in a sample or for the immunoaffinity or affinity chromatography purification of VH3-15 polypeptides from serum or from other biological materials.

More specifically, the various immunoassay methods of the present invention employ the use of anti-VH3-15 idiotypic antibody materials of this invention as an immunochemical reagent to form an immunocomplex with any VH3-15 polypeptide which might be present in a sample. In this manner the presence, absence or amount of VH3-15 polypeptide in a sample is easily detected by assaying for the amount of immunocomplex, either directly or indirectly. Alternatively, the formation of immunocomplex can be exploited as a technique for purification of VH3-15 polypeptides.

Of course, one of skill in the art will appreciate that there are various heterogenous and homogenous protocols, either competitive or noncompetitive, solution-phase or solid-phase, which can be employed in performing an assay method of this invention. Thus, while exemplary assay methods are described herein, the invention is not so limited.

In one embodiment of the present invention there is provided a method of detecting the presence absence or amount of a VH3-15 polypeptide in a sample, comprising (a) contacting a sample with the detectable anti-VH3-15 idiotypic antibody material under conditions suitable to form an immune complex of anti-VH3-15 idiotypic antibody material and VH3-15 polypeptide, and (b) assaying for the presence or amount of VH3-15-containing complex by detecting bound anti-VH3-15 idiotypic antibody material. Preferably, the assay step includes or is followed by comparison of the results to a control to assure accuracy. The term "immune complex" as used herein refers to the product of a specific binding reaction such as for example that between an antigen and its antibody.

In yet another embodiment of the invention, any immune complex formed in step (a) is separated from the remaining sample and VH3-15 polypeptide prior to assaying for the presence or amount of VH3-15 polypeptide-containing complex.

In accordance with the compositions and methods of the present invention, anti-VH3-15 antibody material can be labeled with a detectable marker to create detectable anti-VH3-15 idiotypic antibody material. Methods of labeling the compositions of the present invention (antibodies, nucleic acids and the like) is well known in the art and contemplated as within the scope of the present invention. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981) incorporated herein by reference. The techniques of protein conjugation or coupling through activated functional groups are applicable (See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493,795 all of which are incorporated herein by reference.) and the specific use of biotin/avidin for labeling the compositions of the present invention is exemplified.

As used herein, the word "marker" in its various grammatical forms refer to single atoms and molecules that are either directly or indirectly involved in the production of a detectable signal to indicate the presence of a complex. Any marker can be linked to or incorporated in an expressed protein, polypeptide fragment, or antibody molecule that is part of an antibody or monoclonal antibody composition of the present invention, or used separately. These atoms or molecules can be used alone or in conjunction with additional reagents. Such labels are themselves well-known in clinical diagnostic chemistry and constitute a part of this invention only insofar as they are utilized with otherwise novel proteins, methods, and/or systems.

The detectable marker can be a fluorescent labeling agent that chemically binds to antibodies of antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB-200-SC) and the like. A description of immunofluorescence analysis techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

Radioactive elements are also useful detectable markers. An exemplary radiolabeling agent is a radioactive element that produces gamma ray emissions. Elements which themselves emit gamma rays, such as $^{124}I$, $^{125}I$, $^{126}I$, $^{131}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$indium or $^3H$.

In one embodiment, the detectable marker is an enzyme, such as horseradish peroxidase (HRP), glucose oxidase, and the like. In such cases where the detectable marker is an enzyme such as MRP or glucose oxidase, additional reagents are required to visualize the fact that an immune complex has formed. Such additional reagents for HRP include hydrogen peroxide and an oxidation dye precursor such as diaminobenzidine, o-phenylenediamine dihyrochloride and the like. An additional reagent useful with glucose oxidase is 2,2'-azino-di-(3-ethyl-benzthiazoline-G-sulfonic acid). Depending on the nature of the label or catalytic signal producing system used, a signal can be detected by irradiating the complexed test sample with light and observing the level of fluorescence; by contacting the complexed sample with a substrate which can be catalytically converted by the label to produce a dye, fluorescence or chemiluminescence, in which the formation of dye can be observed visually or in a spectrophotometer; fluorescence can be observed visually or in a fluorometer; or, in the case of chemiluminescence or a radioactive label, by employing a radiation counter such as a gamma counter or gamma emitting markers such as iodine-125. For detection of enzyme-catalyzed markers when the presently preferred combination of HRP is used as the enzyme and o-phenylenediamine dihydrochloride as the substrate, a quantitative analysis of complex can be made using a spectrophotometer, for example a EMAXMicroplate Reader (available from Molecular Devices, Menlo Park, Calif.), at 405 nm in accordance with the manufacturer's instructions.

Specific binding agent are also useful as detectable markers. A "specific binding agent" is a molecular entity capable of selectively binding anti-VH3-15 idiotypic antibody material, VH3-15 polypeptides or the nucleic acids of the present invention or a complex containing these, but which is not itself a polypeptide or antibody molecule composition of the present invention. Exemplary specific binding agents are secondary antibody molecules (e.g., anti-Ig antibodies), complement proteins or fragments thereof, S. aureus protein A, and the like which may themselves be labeled with a detectable marker. If one or more specific binding agents, in the form of secondary antibody molecules, each secondary antibody molecule is preferably species-specific for the antibody or antigen binds.

In yet another embodiment of the present invention, there is provided a method of purifying or isolating VE3-15 polypeptide comprising contacting a sample containing VH3-15 polypeptide with anti-VH3-15 idiotypic antibody material under conditions suitably to form a complex of anti-VH3-15 idiotypic antibody material, and then separating any unbound sample from any complex that formed.

In preferred embodiments of the present invention, anti-VH3-15 idiotypic antibody material is immobilized on a solid substrate. The solid substrate can be any support useful in immunometric assays. The substrate can be made from natural or synthetic material which is insoluble in water and can be rigid or non-rigid. However, the substrate should not significantly affect the desired activity of the antibody material. Preferred substrates include glass slides, test wells made from polyethylene, polystyrene, nylon, nitrocellulose, glass and the like. Also useful are test tubes, filter paper, filtering devices such as glass membranes, beads, and particulate materials such as agarose, cross-linked dextran and other polysaccharides, and the like.

The separation steps for the various assay formats described herein, including removing any unbound sample from the complex, can be performed by methods known in the art. When appropriate, a simple washing with a suitable buffer followed by filtration or aspiration is sufficient. If the antibody material is immobilized on a particulate support, as in the case of microparticles for example, it may be desirable to centrifuge the particulate material, followed by removal of wash liquid. If the antibody material is immobilized on membranes or filters, applying a vacuum or liquid absorbing member to the opposite side of the membrane or filter allows one to draw the wash liquid through the membrane or filter.

The methods of the present invention are normally carried out at or below room temperature at about physiological pH. Because the methods involve the use of proteins, substantially higher temperatures acidity or alkalinity which would substantially modify the tertiary and quaternary structures of the proteins should be avoided. Accordingly, conditions suitable for performing the methods of the present invention generally range from about 1° C. to about 37° C., at about physiological pH.

The present invention also encompasses nucleic acid molecules encoding anti-VH3-15 idiotypic antibody material of the present invention. This invention also encompasses nucleic acid molecules characterized by conservative changes in coding regions that do not alter the phenotype of the polypeptide produced therefrom when compared to the nucleic acid molecule described hereinabove. This invention further encompasses nucleic acid probes of at least 30 nucleotides capable of specifically hybridizing with a sequence included within the sequence of a nucleic acid encoding the anti-VH3-15 idiotypic antibody materials of the present invention.

As used herein, "specifically hybridizing" means the ability of a nucleic acid to recognize a sequence of nucleic acids complementary to its own and to form double-helical segments through hydrogen bonding between the complementary base pairs. Nucleic acid probe technology is well-known to those skilled in the art, who readily appreciate that such probes may vary greatly in length, and accordingly, can hybridize under both nonstringent and stringent conditions to the nucleic acid molecule of the subject invention. One example of stringent hybridization includes incubation of the nucleic acid(s) with the probe in a solution comprising 50% formamide, 5× SSPE (NaCl, NaH$_2$PO$_4$,EDTA), 1× Denhardt's, 0.1% SDS and single stranded salmon sperm DNA at 42° C. Nonstringent hybridization is performed similarly, using a lower concentration, i.e., 35%, of formamide. Alternatively, the utilization of formamide can be obviated, by modifications well known to a skilled artisan, for example, increasing the temperature at which the hybridization is performed. A person of skill in the art is familiar with the various manipulations which can be applied to hybridization conditions in order to obtain optimal results.

As used herein, the term "nucleic acid" encompasses RNA as well as single and double-stranded DNA and cDNA. In addition, as used herein, the term "polypeptide" encompasses any naturally occurring allelic variant thereof as well as man-made recombinant forms.

This invention provides an isolated nucleic acid molecule encoding an anti-VH3-15 idiotypic antibody material. As used herein, the term "isolated nucleic acid molecule" means a nucleic acid molecule that is in a form that does not occur in nature. One means of isolating a nucleic acid sequence encoding anti-VH3-15 idiotypic antibody material is to probe a mammalian cDNA expression library with a natural or artificially designed antibody to anti-VH3-15 idiotypic antibody material encoding nucleic acids using methods well known in the art (see, for example, Ausubel et al., supra 1993). DNA and cDNA molecules which encode mammalian anti-VH3-15 idiotypic antibody material can be used to obtain complementary genomic DNA, cDNA or RNA from human or other mammalian sources.

The invention further provides the above-described isolated nucleic acid molecules operatively linked to a promoter, as well as other regulatory sequences. As used herein, the term "operatively linked" means positioned in such a manner that the promoter will direct the transcription of RNA from the nucleic acid molecule. Examples of such promoters are SP6, T4 and T7.

Vectors which contain both a promoter and a cloning site into which an inserted piece of DNA is operative linked to that promoter are well known in the art. Preferably, these vectors are capable of transcribing RNA in vitro or in vivo. Examples of such vectors are the pGEM series (Promega Biotech, Madison, Wis.). This invention also provides a vector comprising an isolated nucleic acid molecule such as DNA, cDNA or RNA encoding an anti-VH3-15 idiotypic antibody material. Examples of additional vectors useful herein are viruses, such as bacteriophages, baculoviruses and retroviruses, cosmids, plasmids, and the like. Nucleic acid molecules are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers that correspond to a restriction site in the vector DNA, can be ligated to the insert DNA which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are available and can readily be accessed by those of skill in the art.

Also provided are expression vectors comprising a DNA molecule encoding an anti-VH3-15 idiotypic antibody material adapted for expression in a bacterial cell, a yeast cell, a mammalian cell and other animal cells. The vectors additionally comprise the regulatory elements necessary for expression of the DNA in the bacterial, yeast, mammalian or animal cells so located relative to the DNA encoding the antibody material as to permit expression thereof. Regulatory elements required for expression include promoter sequences to bind RNA polymerase and transcription initiation sequences for ribosome binding. For example, a bacterial expression vector includes a promoter such as the lac promoter and for transcription initiation, the Shine-Dalgarno sequence and the start codon AUG (Ausubel et al., supra 1993). Similarly a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the polypeptide.

This invention provides a mammalian cell containing cDNA encoding a mammalian anti-VH3-15 antibody material. An example is a mammalian cell comprising a plasmid adapted for expression in a mammalian cell. The plasmid contains cDNA encoding antibody material and the regulatory elements necessary for expression of the polypeptide. Various mammalian cells may be utilized as hosts, including for example, mouse fibroblast cell NIH3T3, CHO cells, HeLa cells, Ltk- cells, etc. Expression plasmids such as those described above can be used to transfect mammalian cells by methods well known in the art, for example, calcium phosphate precipitation, DEAE-dextran, electroporation, microinjection, lipofection, and the like.

The present invention also provides kits for detecting the presence, absence or amount of VH3-15 polypeptide in a sample. The present invention also provides kits for detecting the presence, absence or amount of nucleic acid encoding anti-VH3-15 idiotypic antibody material in a sample. A suitable kit includes, in an amount sufficient for at least one assay, anti-VH3-15 idiotypic antibody material or nucleic acid probe for anti-VH3-15 idiotypic antibody material as a separately packaged reagent and, preferably a detactable marker and a control VH3-15 polypeptide or VH3-15 nucleic acid sequence, respectively. Instructions for use of the packaged reagent are also typically included.

As used herein, the term "package" refers to a solid matrix or material such as glass, plastic, paper, foil and the like capable of holding within fixed limits antibody material, polypeptide, nucleic acid probe, or nucleic acid sequence of the present invention. Thus, for example, a package can be a glass vial used to contain milligram quantities of a contemplated protein or polypeptide fragment, or it can be a microtiter plate well to which microgram quantities of a contemplated protein or polypeptide fragment have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a kit for assaying for the presence, absence or amount of VH3-15 polypeptide in a sample, such as blood, plasma, or serum, comprises a package containing at least one anti-VH3-15 idiotypic antibody. In addition, the kit preferably includes a detectable marker, as described above, which is capable of signaling the formation of an immune complex containing the anti-VH3-15 idiotypic antibody.

The kits can also include, preferably as a separate package, a specific binding agent as defined above.

The kits can be used in an "ELISA" format to detect the presence, absence or amount of VH3-15 polypeptide in a sample such as blood, serum, or plasma or the presence, absence or amount of nucleic acid encoding anti-VH3-15 idiotypic antibody in a sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090, U.S. Pat. No. 3,850,752; and U.S. Pat. No. 4,016,043, which are all incorporated herein by reference.

Thus, an anti-VH3-15 idiotypic antibody or nucleic acid probe can be affixed to a solid matrix to form a solid support that comprises a package in the subject diagnostic systems. A reagent is typically affixed to a solid matrix by adsorption from an aqueous medium although other modes of affixation applicable to polypeptides and nucleic acids well known to those skilled in the art can be used.

Useful solid matrices are also well known in the art. Such materials are water insoluble and include the cross-linked dextran available under the trademark from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The anti-VH3-15 idiotypic antibodies, labeled specific binding agent, VH3-15 polypeptides, nucleic acid probes or VH3-15 nucleic acid molecules of any kit described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this kit.

The packaging materials discussed herein in relation to the kits are those customarily utilized in kits and commercially available. The term "package" refers to a solid matrix or material such as glass, plastic (e.g., polyethylene, polypropylene and polycarbonate), paper, foil and the like capable of holding within fixed limits a diagnostic reagent such a protein, polypeptide fragment, antibody or monoclonal antibody of the present invention. Thus, for example, a package can be a bottle, vial, plastic and plastic-foil laminated envelope or the like container used to contain a contemplated a reagent or it can be a microtiter plate well to which microgram quantities of a contemplated reagents have been operatively affixed, i.e., linked so as to be capable of being immunologically bound by an antibody or polypeptide to be detected.

The invention will now be described in greater detail by reference to the following non-limiting examples.

EXAMPLES

Statistical analysis. Two-tailed paired Student's t-test values were calculated using Statview™ on a Macintosh II™ computer.

Example I

Production of Anti-VH3-15 Hybridomas

Monoclonal antibodies specific for VH3-15 polypeptides can be produced using standard hybridoma techniques, i.e., immunizing a mammal with a VH3-15 polypeptide, fusing B lymphocytes from the immunized animal with immortalized cells to produce hybridomas and then screening the hybridomas for antibodies that bind the immunogen. Representative VH3-15 polypeptides are provided in SEQ ID NO. 2 through 4. SEQ ID NO. 1 represents an example of a VH3-15 nucleic acid sequence. The germline VH3-15 nucleic acid sequence is available from Genbank. Any one or all of these polypeptides may be used as an immunogen.

Alternatively, other VH3-15 polypeptides may be created for use as immunogens from the given sequences by substitution, addition or deletion of one or more amino acids. Another alternative is to use other known VH 3-15 amino acid sequence as immunogens such as, for example LJ11, LJ67. LJ23 as described in Braun, et al., *J. Clin. Invest.*, 89:1395–1402 (1992).

The nucleic acid sequence encoding LJ86 (Genbank Accession No. M82929) was subcloned into the pGEX bacterial expression system (catalog no. 27-4570-01, Pharmacia Biotech, Inc., Piscataway, N.J.) to produce a VH3-15/glutathione-S-transferase fusion protein and the fusion protein purified all in accordance with the manufacturer's instructions.

This material was then used to immunize Balb/c mice, from which hybridomas were produced and screened for IgM and IgG antibodies reacting with the VH3-15 fusion protein immunogen. More specifically, primary immunization of Balb/c mice was carried out with 10 micrograms purified VH3-15 immunogen by intrasplenic injection. See, Spitz, et al. *J. Immunol. Methods*, 70:39–43 (1984), incorporated herein by reference in its entirety. Four days later, spleen cells were harvested for fusion.

Spleenocytes from immunized animals were prepared and fused with NS-1 cell (ATCC Accession No. TIB18) as described, for example in Harlow and Lane, *Antibodies: A Laboratory Manual* (Cold Spring Harbor Laboratory 1988). Hybrids were selected by use of medium containing hypoxanthine, aminopterin and thymidine ("HAT medium") two days after fusion. Surviving hybrids were transferred to micotitre culture plates and medium supernates assessed for specific reactivity with the VH3-15 immunogen. Positive hybridomas were subcloned twice in microtitre plates and selected by ELISA for VH3-15 reactivity using peroxidase-anti-mouse Ig. (Southern Biotech Assoc., Birmingham, Ala.) Among 600 hybridomas screened, nine produced monoclonal antibodies specific for the VH3-15 immunogen. Six of these nine hybridoma cell lines are stored in liquid nitrogen by Dr. Jonathan Braun in room 4-557 of the McDonald Research Medical Laboratory located at 675 Circle Drive South Los Angeles, Calif. 90024. These six hybridoma cell lines are labeled and identified by the following laboratory names:

NS2B9D7E6F5 (and also known as BK1)
NS5A4D3F4F9 (and also known as BK2)
NS5B7F3F6E1 (and also known as BK3)
NS1H6C1D4B3 (and also known as BK4)
NS1H6B9D6 (and also known as BK5)
NS5B7F3F6E1 (and also known as BK7)

Of these, a number are IgM and IgG producing hybridomas and BK2 is an IgG,kappa producing hybridoma. On Sep. 26, 1994, the BK2 hybridoma was deposited with the American Type Culture Collection (ATCC) depository at 12301 Parklawn Drive, Rockville, Md. 20852, and assigned accession number HB 11720.

Larger amounts of monoclonal antibody were obtained by inoculating Balb/c mice interperitoneally with $1 \times 10^7$ cells/animal. Ascites protein was purified by ammonium sulphate precipitation and DEAE-Sephacel chromatography, and in some cases biotinylated with NHS-LC-biotin (Pierce, Rockford, Ill.) following manufacturer's recommendations.

Example II

ELISA for Screening Hybridomas for Anti-VH3-15 Idiotypic Monoclonal Antibody Production Specificity of monoclonal antibodies for VH3-15 polypeptides can be determined by a standard ELISA method described in Berberian, et al., *Science*, 261:1588–1591 (1993), incorporated herein by reference in its entirety. Briefly, ELISA plate wells were coated with various concentrations of either a known VH3-15 antibody or a known non-VH3-15 antibody. For each hybridoma being screened, monoclonal antibodies derived from the hybridoma were added to VH3-15 antibody and non-VH3-15 antibody coated wells. Specificity was detected by enzymatic digestion of substrate using peroxidase anti-mouse Ig.

More specifically, LSF2 is a human anti-*Hemophilus influenza* monoclonal antibodies encoding VH3-15 and is described in Adderson, et al., *J. Immunol.*, 147:1667–1674 (1991). In the following ELISA, LSF2 was used as an VH3-15 antibody. 477 is a human monoclonal antibody to Waldenstrom's paraproteins encoding VH3-30 and is described in Axelrod, et al., *Blood*, 77:1484–1490 (1991)). In the following ELISA, 477 was used as the non-VH3-15 antibody.

1 to 10,000 ng of VH3-15 antibody or non-VH3-15 antibody per well (or preferably 10 to 1000 ng. or even more preferably 20 ng) were diluted in 50 μL carbonate-bicarbonate buffer, pH 9.6 (Sigma, St. Louis, Mo.), added to microtiter plates (Costar, Pleasanton, Calif.), and incubated overnight at 4° C. The plates were washed 3 times for 15 minutes each with phosphate-buffered saline+0.5% "TWEEN 20" (polyoxyethylenesorbitan monolaurate). (ELISA buffer) and blocked for 30 minutes in ELISA buffer.

Monoclonal antibodies from each hybridoma being screened were reacted against VH3-15 antibody and against non-VH3-15 antibody by adding 50 µL of monoclonal antibody (diluted 1:1000 in ELISA buffer) to sample wells and incubated for 1 hour at 4° C. Plates were washed five times with "TWEEN 20" in PBS (0.05% polyoxyethylenesorbitan monolaurate in PBS) at room temperature for one minute per wash.

Monoclonal antibody specificity was detected by enzymatic digestion of substrate. Each well was incubated for one hour at 4° C with 1:10,000 goat anti-mouse IgG horseradish peroxidase (Caltag, San Francisco, Calif.) and washed five times with "TWEEN 20" in PBS (0.05% polyoxyethylenesorbitan monolurate in PBS) at room temperature for one minute per wash.

Each well was then incubated with o-phenylenediamine dihydrochloride (Sigma) for 30 minutes at 37° C. 3 N $H_2SO_4$ was added to stop the reaction. Optical density was determined by absorbance at 492 nm and ranged from 0 to 0.8 optical density units. (OD range in correspondence with 1–10,000 ng Ab used.) It is recommended that an absorbance reading two times the background be considered positive binding to antibody. Non-coated wells were used as the control. Monoclonal antibodies which bind VH3-15 antibody are considered an anti-VH3-15 idiotypic monoclonal antibody. Their specificity is confirmed by their lack of binding with non-VH3-15 antibody.

Using the foregoing assay, it can be shown that monoclonal antibodies produced in accordance with the present invention distinguish between the following VH3 gene products: VH3-30, VH3-23, and VH3-15. BK2 produced mAb which were strongly reactive with the VH3-15 antibody (LSF2), but were unreactive with non-VH3-15 antibody Conversely, B6 and D12 (known anti-VH3-30 idiotypic monoclonal antibodies) were reactive with non-VH3-15 antibody (477), but unreactive with VH3-15 antibody (LSF2). 16/6 (a known anti-VH3-23 idiotypic monoclonal antibody, Young, et al., *J. Immunol.*, 145:2545–2553 (1990)) reacted with neither VH3-15 antibody (LSF2) nor non-VH3-15 antibody (477). BK2 lacked detectable reactivity with polyclonal human IgM and IgG.

These findings demonstrated that BK2 selectively bound to VH3-15 antibody (versus other closely related VH3 family gene products), and lacked reactivity with prevalent sequences such as heavy or light chain constant regions. The apparent paucity of serum VH3-15 was consistent with the infrequent use of this gene, compared to other VH3 genes, in cDNA libraries prepared from polyclonal human B cell populations.

Although the invention has been described with reference to presently preferred embodiments, it should be understood that various modifications can be made without departing from the spirit of the invention.

I claim:

1. A BK2 hybridoma having ATCC accession number HB 11720.

2. An antibody molecule produced by the hybridoma of claim 1, or antibody material derived therefrom.

3. The antibody material of claim 2, labeled with a detectable marker.

4. Antibody material that specifically binds the same idiotope as the antibody molecule produced by the hybridoma of claim 1.

5. Anti-VH3-15 idiotypic antibody material having immunoreactivity with a variable heavy chain segment of a VH3-15 polypeptide.

6. A hybridoma cell from which the anti-VH3-15 idiotypic antibody material of claim 5 is derived.

7. The antibody material of claim 5, wherein the VH3-15 polypeptide comprises an LSF2 anti-*Haemophilus influenzae* type b capsular polysaccharide antibody.

8. The antibody material of claim 5, wherein the antibody material is selected from a group consisting of an antibody molecule, a F(ab')$_2$ and a Fab.

9. A kit for detecting a VH3-15 polypeptide in a sample, comprising the anti-VH3-15 idiotypic antibody material of claim 5 and packaging material.

10. The kit of claim 9, wherein the anti-VH3-15 idiotypic antibody material is a monoclonal antibody that binds the same idiotope as the monoclonal antibody produced by a BK2 hybridoma having ATCC accession number HB 11720.

* * * * *

UNITED STATES PATENT AND TRADEMARK OFFICE
CERTIFICATE OF CORRECTION

PATENT NO. : 5,738,847
DATED : Apr. 14, 1998
INVENTOR(S) : Jonathan Braun

It is certified that error appears in the above-identified patent and that said Letters Patent is hereby corrected as shown below:

Column 2, line 45, please delete "their energy." and replace therefor with --their anergy.--.

Column 2, line 66, please delete "cDNA therefor" and replace therefor with --cDNA are--.

Column 4, line 21, please delete "20 pl," and replace therefor with --20pl,--.

Column 7, line 37, please delete "presence absence" and replace therefor with --presence, absence,--.

Column 8, line 48, please delete "MRP" and replace therefor with --HRP--.

Column 10, line 57, please delete "operative linked" and replace therefor with --operatively linked--.

Column 11, line 67, please delete "detactable" and replace therefor with --detectable--.

UNITED STATES PATENT AND TRADEMARK OFFICE
CERTIFICATE OF CORRECTION

PATENT NO. : 5,738,847
DATED : Apr. 14, 1998
INVENTOR(S) : Jonathan Braun

It is certified that error appears in the above-identified patent and that said Letters Patent is hereby corrected as shown below:

Column 13, line 13, please delete "such a protein," and replace therefor with --such as a protein,--.

Column 13, line 17, please delete "a reagent" and replace therefor with --reagent--.

Column 13, line 18, please delete "reagents" and replace therefor with --reagent--.

Column 16, line 10, please delete "body Conversely," and replace therefor with --body (477). Conversely,--.

Column 16, line 21, please delete "prevalent" and replace therefor with --prevalent Ig--.

Signed and Sealed this

Tenth Day of April, 2001

*Attest:*

NICHOLAS P. GODICI

*Attesting Officer*   Acting Director of the United States Patent and Trademark Office

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 501 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 161..460

( i x ) FEATURE:
        ( A ) NAME/KEY: intron
        ( B ) LOCATION: group(47..149, 470..492)

( i x ) FEATURE:
        ( A ) NAME/KEY: misc_feature
        ( B ) LOCATION: 247..261
        ( D ) OTHER INFORMATION: /function="Structural domain of
            protein product"
        / product="Complement Determing Region I - CDRI"

( i x ) FEATURE:
        ( A ) NAME/KEY: misc_feature
        ( B ) LOCATION: 308..364
        ( D ) OTHER INFORMATION: /function="Structural domain of
            protein product"

/ product="Complement Determining Region II - CDR II"

( x i ) SEQUENCE DESCRIPTION: SEQ ID NO:1:

| | | | | | | |
|---|---|---|---|---|---|---|
| ATGGAGTTTG | GGCTGAGCTG | GATTTCCTT | GCTGCTATTT | TAAAAGGTGA | TTTATGGAGA | 60 |
| ACTAGAGAGA | TTAAGTGTGA | GTGAACGTGA | GTGAGAGAAA | CAGTGGATAT | GTGTGGCAGT | 120 |
| TTCTGAACTT | AGTGTCTCTG | TGTTTGCAGG | TGTCCAGTGT | GAG GTG CAG | CTG GTG | 175 |
| | | | | Glu Val Gln | Leu Val | |
| | | | | 1 | 5 | |

| GAG | TCT | GGG | GGA | GGC | TTG | GTA | AAG | CCT | GGG | GGG | TCC | CTT | AGA | CTC | TCC | 223 |
|---|---|---|---|---|---|---|---|---|---|---|---|---|---|---|---|---|
| Glu | Ser | Gly | Gly | Gly | Leu | Val | Lys | Pro | Gly | Gly | Ser | Leu | Arg | Leu | Ser | |
| | | | 10 | | | | | 15 | | | | | 20 | | | |

| TGT | GCA | GCC | TCT | GGA | TTC | ACT | TTC | AGT | AAC | TCC | TCG | ATG | AGC | TGG | GTC | 271 |
|---|---|---|---|---|---|---|---|---|---|---|---|---|---|---|---|---|
| Cys | Ala | Ala | Ser | Gly | Phe | Thr | Phe | Ser | Asn | Ser | Ser | Met | Ser | Trp | Val | |
| | | | 25 | | | | 30 | | | | | 35 | | | | |

| CGC | CAG | GCT | CCA | GGG | AAA | GGG | CTG | GAG | TGG | GTT | GGC | CGT | ATT | AAA | AGC | 319 |
|---|---|---|---|---|---|---|---|---|---|---|---|---|---|---|---|---|
| Arg | Gln | Ala | Pro | Gly | Lys | Gly | Leu | Glu | Trp | Val | Gly | Arg | Ile | Lys | Ser | |
| | | 40 | | | | | 45 | | | | | 50 | | | | |

| AAA | ACT | GAT | GGT | GGG | ACA | ACA | GAC | TAC | GCT | GCA | CCC | GTG | AAA | GGC | AGA | 367 |
|---|---|---|---|---|---|---|---|---|---|---|---|---|---|---|---|---|
| Lys | Thr | Asp | Gly | Gly | Thr | Thr | Asp | Tyr | Ala | Ala | Pro | Val | Lys | Gly | Arg | |
| | 55 | | | | | 60 | | | | | 65 | | | | | |

| TTC | ACC | ATC | TCA | AGA | GAT | GAT | TCA | AAA | AAC | TCA | CTG | TAT | CTG | CAA | ATG | 415 |
|---|---|---|---|---|---|---|---|---|---|---|---|---|---|---|---|---|
| Phe | Thr | Ile | Ser | Arg | Asp | Asp | Ser | Lys | Asn | Ser | Leu | Tyr | Leu | Gln | Met | |
| 70 | | | | | 75 | | | | | 80 | | | | | 85 | |

| AAC | AGC | CTG | AAA | ACC | GAG | GAC | ACA | GCC | GTG | TAT | TAC | TGT | ACC | ACA | | 460 |
|---|---|---|---|---|---|---|---|---|---|---|---|---|---|---|---|---|
| Asn | Ser | Leu | Lys | Thr | Glu | Asp | Thr | Ala | Val | Tyr | Tyr | Cys | Thr | Thr | | |
| | | | 90 | | | | | 95 | | | | | | 100 | | |

| | | | |
|---|---|---|---|
| GACACAGCGA | GGGGAGGTCA | GTGTGAGCCC | GGACACAAAC C | 501 |

( 2 ) INFORMATION FOR SEQ ID NO:2:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Ser |
|---|---|---|---|---|---|---|---|---|---|---|---|---|---|---|---|
| | | | 20 | | | | | 25 | | | | | 30 | | |

| Ser | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Arg | Ile | Lys | Ser | Lys | Thr | Asp | Gly | Gly | Thr | Thr | Asp | Tyr | Ala | Ala |
|---|---|---|---|---|---|---|---|---|---|---|---|---|---|---|---|
| | 50 | | | | | 55 | | | | | 60 | | | | |

| Pro | Val | Lys | Gly | Arg | Phe | Thr | Ile | Ser | Arg | Asp | Asp | Ser | Lys | Asn | Ser |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Thr | Thr |
|---|---|---|---|
| | | | 100 |

( 2 ) INFORMATION FOR SEQ ID NO:3:

( i ) SEQUENCE CHARACTERISTICS:
        ( A ) LENGTH: 100 amino acids
        ( B ) TYPE: amino acid
        ( C ) STRANDEDNESS: single
        ( D ) TOPOLOGY: unknown (  i i  ) MOLECULE TYPE: peptide (  v  ) FRAGMENT TYPE: N-terminal (  i x  ) FEATURE:
   ( A ) NAME/KEY: Region
   ( B ) LOCATION: 31..36
   ( D ) OTHER INFORMATION: /label=CDRI
     / note="Complement Determining Region I"

(  i x  ) FEATURE:
   ( A ) NAME/KEY: Region
   ( B ) LOCATION: 50..69
   ( D ) OTHER INFORMATION: /label=CDRII
     / note="Complement Determining Region II"

(  x i  ) SEQUENCE DESCRIPTION: SEQ ID NO:3:

```
Glu Val Gln Leu Val Glu Ser Gly Gly Gly Leu Val Lys Pro Gly Arg
 1               5                  10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Ala Glu Asp Thr Ala Val Tyr
                85                  90                  95

Tyr Cys Thr Thr
            100
```

( 2 ) INFORMATION FOR SEQ ID NO:4:

(  i  ) SEQUENCE CHARACTERISTICS:
   ( A ) LENGTH: 125 amino acids
   ( B ) TYPE: amino acid
   ( C ) STRANDEDNESS: single
   ( D ) TOPOLOGY: unknown (  i i  ) MOLECULE TYPE: peptide (  v  ) FRAGMENT TYPE: N-terminal (  i x  ) FEATURE:
   ( A ) NAME/KEY: Region
   ( B ) LOCATION: 28..33
   ( D ) OTHER INFORMATION: /label=CDRI
     / note="Complement Determining Region I"

(  i x  ) FEATURE:
   ( A ) NAME/KEY: Region
   ( B ) LOCATION: 47..66
   ( D ) OTHER INFORMATION: /label=CDRII
     / note="Complement Determining Region II"

(  i x  ) FEATURE:
   ( A ) NAME/KEY: Region
   ( B ) LOCATION: 98..125
   ( D ) OTHER INFORMATION: /label=CDRIII
     / note="Complement Determining Region III"

(  x i  ) SEQUENCE DESCRIPTION: SEQ ID NO:4:

```
Leu Val Glu Ser Arg Gly Gly Leu Val Lys Pro Gly Arg Ser Leu Arg
 1               5                  10                  15

Leu Ser Cys Ala Ala Ser Gly Phe Thr Phe Ser Asn Ala Trp Met Ser
                20                  25                  30

Trp Val Arg Gln Ala Pro Gly Lys Gly Leu Glu Trp Val Gly Arg Ile
```

|   |   |   | | 35 | | | 40 | | | | | 45 | | | |
|---|---|---|---|---|---|---|---|---|---|---|---|---|---|---|---|
| Lys | Ser 50 | Lys | Thr | Asp | Gly | Gly 55 | Thr | Thr | Asp | Tyr | Ala 60 | Ala | Pro | Val | Lys |
| Gly 65 | Arg | Phe | Thr | Ile | Ser 70 | Arg | Asp | Asp | Ser | Lys 75 | Asn | Thr | Leu | Tyr | Leu 80 |
| Gln | Met | Asn | Ser | Leu 85 | Lys | Ala | Glu | Asp | Thr 90 | Ala | Val | Tyr | Tyr | Cys 95 | Thr |
| Thr | Trp | Tyr | Pro 100 | Asp | Ile | Leu | Asp | Ser 105 | Cys | Tyr | Ala | Ser | Tyr 110 | Phe | Asp |
| Tyr | Trp | Gly 115 | Gln | Gly | Thr | Leu | Val 120 | Thr | Val | Ser | Ser | Gly 125 | | | |